United States Patent [19]

Scholz

[11] Patent Number: 5,908,619

[45] Date of Patent: Jun. 1, 1999

[54] HYDROALCOHOLIC COMPOSITIONS THICKENED USING SURFACTANT/POLYMER COMPLEXES

[75] Inventor: Matthew T. Scholz, Woodbury, Minn.

[73] Assignee: Minnesota Mining and Manufacturing Company, St. Paul, Minn.

[21] Appl. No.: 08/781,091

[22] Filed: Jan. 9, 1997

[51] Int. Cl.$^6$ .......................... A61K 9/08; A61K 47/30; A61K 7/48

[52] U.S. Cl. .................. 424/78.02; 424/78.07; 514/772.4; 514/772.3; 514/772.6

[58] Field of Search .......................... 424/78.02

[56] References Cited

U.S. PATENT DOCUMENTS

| | | | |
|---|---|---|---|
| 2,054,989 | 9/1936 | Moore | 167/58 |
| 2,153,143 | 4/1939 | Figg, Jr. et al. | 87/5 |
| 2,678,902 | 5/1954 | Mehaffey | 167/91 |
| 3,131,152 | 4/1964 | Klausner | 252/305 |
| 3,131,153 | 4/1964 | Klausner | 252/305 |
| 3,395,214 | 7/1968 | Mummert | 424/47 |
| 3,415,939 | 12/1968 | Minton | 424/357 |
| 3,840,465 | 10/1974 | Knowles et al. | 252/90 |
| 4,006,218 | 2/1977 | Sipos | 424/54 |
| 4,199,564 | 4/1980 | Silver et al. | 421/80 |
| 4,202,881 | 5/1980 | Gross et al. | 424/70 |
| 4,254,104 | 3/1981 | Suzuki | 424/170 |
| 4,464,293 | 8/1984 | Dobrin | 252/547 |
| 4,478,853 | 10/1984 | Chaussee | 424/358 |
| 4,501,834 | 2/1985 | Su | 524/28 |
| 4,511,486 | 4/1985 | Shah | 252/90 |
| 4,542,012 | 9/1985 | Dell | 424/28 |
| 4,559,226 | 12/1985 | Fogel et al. | |
| 4,584,192 | 4/1986 | Dell et al. | 424/81 |
| 4,671,957 | 6/1987 | Holtshousen | 424/80 |
| 4,695,453 | 9/1987 | Tuominen et al. | 424/81 |
| 4,719,239 | 1/1988 | Muller et al. | 514/23 |
| 4,752,612 | 6/1988 | Saito et al. | 514/420 |
| 4,806,262 | 2/1989 | Snyder | 252/90 |
| 4,831,023 | 5/1989 | Garlen et al. | |
| 4,839,167 | 6/1989 | Yamamoto et al. | 424/71 |
| 4,883,660 | 11/1989 | Blackman et al. | |
| 4,915,934 | 4/1990 | Tomlinson | 424/45 |
| 4,931,282 | 6/1990 | Asmus et al. | 424/448 |
| 4,956,170 | 9/1990 | Lee | 424/81 |
| 4,957,908 | 9/1990 | Nelson | 514/55 |
| 4,981,678 | 1/1991 | Tomlinson | 424/45 |
| 5,120,716 | 6/1992 | Miyazawa et al. | 514/23 |
| 5,128,123 | 7/1992 | Brewster et al. | 424/65 |
| 5,149,719 | 9/1992 | Ferber et al. | 514/772 |
| 5,164,107 | 11/1992 | Khan et al. | 252/106 |
| 5,167,950 | 12/1992 | Lins | 424/47 |
| 5,180,061 | 1/1993 | Khan et al. | 206/570 |
| 5,180,584 | 1/1993 | Sebag et al. | 424/401 |
| 5,223,261 | 6/1993 | Nelson et al. | 424/443 |
| 5,225,473 | 7/1993 | Duan | 524/388 |
| 5,232,691 | 8/1993 | Lemole | 424/78.02 |
| 5,298,242 | 3/1994 | Vanlerberghe et al. | 424/78.36 |
| 5,334,388 | 8/1994 | Hoang et al. | 424/402 |
| 5,362,484 | 11/1994 | Wood et al. | 514/938 |
| 5,409,966 | 4/1995 | Duan et al. | 522/152 |
| 5,484,597 | 1/1996 | Slavtcheff et al. | 424/401 |
| 5,512,199 | 4/1996 | Khan et al. | 252/106 |
| 5,585,092 | 12/1996 | Trandai et al. | 424/78.02 |
| 5,626,853 | 5/1997 | Bara et al. | 424/401 |

FOREIGN PATENT DOCUMENTS

| | | |
|---|---|---|
| B-72440/87 | 11/1987 | Australia . |
| 0 014 502 A1 | 8/1980 | European Pat. Off. . |
| 0 223 681 A1 | 5/1987 | European Pat. Off. . |
| 0 260 641 A2 | 3/1988 | European Pat. Off. . |
| 0 289 160 A1 | 4/1988 | European Pat. Off. . |
| 0 381 618 A1 | 8/1990 | European Pat. Off. . |
| 0 451 949 A1 | 10/1991 | European Pat. Off. . |
| 0 522 624 A1 | 1/1993 | European Pat. Off. . |
| 0 689 767 A2 | 1/1996 | European Pat. Off. . |
| 0 745 389 A1 | 12/1996 | European Pat. Off. . |
| 788 811 | 10/1935 | France . |
| 2 406 438 | 5/1979 | France . |
| 34 16 777 A1 | 11/1985 | Germany . |
| 36 32 030 A1 | 3/1988 | Germany . |
| 80 92 078 | 4/1996 | Japan . |
| 1 527 781 | 10/1978 | United Kingdom . |
| WO 93/07903 | 4/1993 | WIPO . |
| WO 94/13354 | 6/1994 | WIPO . |
| WO 95/03772 | 2/1995 | WIPO . |
| WO 97/00667 | 1/1997 | WIPO . |

OTHER PUBLICATIONS

BIOSIS Abstract 80:188 400, Abstract of *Zentralbl Bakteriol Parasitenkd Infektionskr Hyg Erst Abt Orig Reihe B Hyg Krankaenhaushyg Betriebshyg Praev Med*, 168, pp. 5–6 (1979).

BIOSIS Abstract 86:434 601, Abstract of *Hyg. Med.*, 11, pp. 238–241 (1986).

Bulletin No. 51–0001–259, Speciality Chemicals of ICI America of Wilmington, DE.

J.L. Cohen et al., "Penetration of 5–Fluorouracil In Excised Skin", *The J. of Investigative Dermatology*, 62, pp. 507–509 (1974).

CTFA Cosmetic Ingredient Handbook, Published by The Cosmetic, Toiletry and Fragrance Association, Inc., pp. 37,64–65,78, 81 (1988).

G.M. Eccleston, "Application of Emulsion Stability Theories to Mobile and Semisolid O/W Emulsions", *Cosmetics & Toiletries*, 101, pp. 73–92 (1986).

G.M. Eccleston, "Influence of long chain alcohols (or acids) and surfactants on the stabilities and consistencies of cosmetic lotions and creams", *Cosmetics and Toiletries*, 92, pp. 21–28 (1977).

E.D. Goodard et al., "Novel gelling structures based on polymer/surfactant systems", *J. Soc. Cosmet. Chem.*, 42, pp. 19–34 (1991).

P.B. Price, "Reevaluation Of Ethyl Alcohol As A Germicide", *Archives of Surgery*, pp. 492–502 (Undated).

R.B. Stoughton, "Vasoconstrictor Activity and Percutaneous Absorption of Glucocorticosteroids", *Arch. Derm.*, 99, pp. 753–756 (1969).

"Textbook of Polymer Science", F.W. Billmeyer, Ed.; Wiley–Interscience, NY; $2^{nd}$ Edition; pp. 84–85 (1971).

*Primary Examiner*—Peter F. Kulkosky
*Attorney, Agent, or Firm*—Gary L. Griswold; Robert W. Sprague; Jeffrey J. Hohenshell

[57] ABSTRACT

Hydroalcoholic compositions and methods of preparation are provided. The composition includes a lower alcohol and water in a weight ratio of at least about 20:80 and a thickener system comprising a complex of at least one charged polymer and at least one oppositely charged surfactant.

46 Claims, No Drawings

5,908,619

HYDROALCOHOLIC COMPOSITIONS THICKENED USING SURFACTANT/POLYMER COMPLEXES

FIELD OF THE INVENTION

The present invention relates to compositions useful as surgical hand preparations and antimicrobial hand lotions. More specifically, the invention relates to stable hydroalcoholic compositions thickened using charged polymers and oppositely charged surfactants.

BACKGROUND OF THE INVENTION

Control of nosocomial infection and exposure to infectious disease is of paramount concern to doctors, nurses, and clinicians who work in hospitals and surgery centers. One of the most effective methods for controlling infection is regimented hand disinfection before and possibly after each patient contact and particularly before and after each surgical procedure. Hand disinfection is generally accomplished using antimicrobial soaps with water. These soaps are usually formulated to include either povidone-iodine (usually 7.5% by weight) or chlorhexidine digluconate (CHG) (usually 2% or 4% by weight) as the active antimicrobial agent. In addition, these formulated soaps may contain surfactants and possibly low levels of humectants such as glycerin.

Hand disinfection is also accomplished using presurgical scrub replacements. These are used instead of the soap and water scrub. Presurgical scrub replacements ideally achieve bacterial kill equal to or better than a traditional soap and water scrub and in a shorter period of time. Additionally, they maintain or improve the skin's natural barrier to microbial and chemical contamination while providing acceptable tactile properties. Examples of presurgical scrub replacements include hydroalcoholic gels which generally include high levels of either ethanol or isopropanol as the disinfecting agent and also include a thickener and optionally a humectant (e.g., glycerin). To date, thickeners used in hydroalcoholic gels have been based on anionic polymers such as polyacrylic acid (sold under the tradename "CARBOPOL" by BF Goodrich Specialty Polymers and Chemicals Division of Cleveland, Ohio). U.S. Pat. No. 4,915,934 (Tomlinson) discloses the use of CHG-containing antiseptic foams based on hydroalcoholic solvents, a fatty alcohol, and a surfactant. The surfactant is selected from the group of ethoxylated sorbitan alkylates, ethoxylated fatty alcohols, and ethoxylated nonyl phenols.

Formulating stable viscous hydroalcoholic emulsions is difficult for two reasons. First, addition of short chain alcohols (such as ethanol) to an aqueous system decreases the surface tension dramatically. For example, 40% by weight ethanol in water has a surface tension of approximately 31 dynes/cm compared to pure water which has a surface tension of about 72 dynes/cm at 20° C. A hydroalcoholic solution at 60% by weight ethanol has a dramatically decreased surface tension as compared to water. Such a composition has a surface tension of approximately 27 dynes/cm at 20° C. Second, many surfactants typically used in cosmetic emulsions become completely or partially soluble in hydroalcoholic systems.

In bulletin 51-0001-259 regarding skin care, Specialty Chemicals of ICI America of Wilmington, Del. state that although ethanol can provide several benefits to skin care emulsions, formulators often avoid ethanol because it is difficult to prepare stable emulsions in its presence. In fact, the bulletin also states that ethanol is often used to break emulsions.

U.S. Pat. No. 4,956,170 (Lee) discloses a hydroalcoholic skin moisturizing/conditioning antimicrobial gel. The gel comprises 60–75% by weight ethanol and 0.4–2% by weight of an anionic carbomer polymeric thickening agent. The formulations also comprise polyethoxylated nonionic surfactants/emulsifiers to stabilize the added emollient oils in addition to a fatty alcohol. U.S. Pat. No. 5,167,950 (Lins) discloses an antimicrobial aerosol mousse having a high alcohol content. The mousse comprises alcohol, water, a polymeric gelling agent and a surfactant system comprising a C16–C22 alcohol, aerosol propellant, and a nonionic polyethoxylated surfactant. These systems are based on neutralized polymeric acrylic acids, which are anionic and therefore incompatible with positively charged molecules such as chlorhexidine digluconate. Furthermore, these systems, while cosmetically acceptable, do not shear thin readily and can feel heavy with a somewhat tacky feel under gloves.

Novel Gelling Agents Based on Polymer/Surfactant Systems, E. D. Goodard et. al., *J. Soc. Cosmet. Chem.*, 42, 19–34 (Jan/Feb. 1991) discloses polymer/surfactant thickener systems for completely aqueous systems based on quaternary polymers in combination with anionic surfactants. These thickener systems, however, are not effective in hydroalcoholic solvent systems.

In other hydroalcoholic systems, such as those described in U.S. patent application Ser. Nos. 08/493,714 and 08/493,695 (both of which were filed on Jun. 22, 1995 and assigned to 3M Company), nonionic, anionic, cationic, or zwitterionic emulsifiers are used as thickeners, without the need for a polymeric thickener such as polyacrylic acid. Although these systems are highly desirable, other high viscosity hydroalcoholic compositions useful as an antimicrobial lotion, for example, are still needed.

SUMMARY OF THE INVENTION

This invention provides compositions useful as products for skin disinfection such as presurgical hand preparations and lotions that are easily washed off hands with water, preferably with no apparent residue. The preferred compositions of this invention, in general, have a very nice feel after both single and multiple applications. Additionally, preferred compositions maintain or improve the skin condition after multiple applications with no slimy or abnormal feeling noticed during post application hand washing. When used as a presurgical scrub replacement, this invention achieves bacterial, fungal, and viral kill equal to or better than a traditional soap and water scrub in a shorter period of time while maintaining or improving the skin's natural barrier to microbial and chemical contaminants. The invention overcomes the shortcomings of past compositions by providing a viscous composition that can include a relatively high concentration of a lower alcohol, but does not require a high molecular weight polymeric thickener to make the composition viscous, which can often result in a slimy feeling once the hands are washed. Further, the composition has a cosmetically elegant feel and may be dispensed as a lotion or as a foam. It may also be suitable for the enhancement of the transdermal delivery of the pharmaceutical agent.

One embodiment of the present invention is a hydroalcoholic composition comprising: (a) a lower alcohol and water in a weight ratio of at least about 20:80; (b) a thickener system comprising a complex of at least one charged polymer and at least one oppositely charged surfactant, wherein the polymer and surfactant are selected such that: (i) the composition has a viscosity greater than that of the same composition with either the polymer or the surfactant absent; and (ii) the composition has a viscosity of at least about 4,000 centipoise at 23° C., when free of auxiliary thickeners. Preferably, the composition is a stable hydroalcoholic composition.

Another embodiment of the invention is a hydroalcoholic composition preparable by combining components comprising: (a) a lower alcohol and water in a weight ratio of at least about 20:80; (b) at least one ionizable polymer; and (c) at least one ionizable surfactant; wherein the polymer and surfactant are selected such that: (i) the hydroalcoholic composition has a viscosity greater than that of the same composition with either the polymer or the surfactant absent; and (ii) the hydroalcoholic composition has a viscosity of at least about 4,000 centipoise at 23° C., when free of auxiliary thickeners.

The present invention also provides methods of preparing the hydroalcoholic compositions of the present invention. One method involves: heating an ionizable surfactant at a sufficient temperature to melt the surfactant; combining an ionizable polymer with a solvent system comprising water; combining the melted surfactant with the polymer/solvent system mixture to form a hydroalcoholic composition comprising a lower alcohol and water in a weight ratio of at least about 20:80; a thickener system comprising a complex of at least one charged polymer and at least one oppositely charged surfactant, wherein the polymer and surfactant are selected such that the composition has a viscosity greater than that of the same composition with either the polymer or the surfactant absent, and has a viscosity of at least about 4,000 centipoise at 23° C., when free of auxiliary thickeners.

DEFINITIONS

"Ambient temperature" as used herein refers to the temperature range of about 21–25° C.

"Auxiliary thickeners" as used herein refers to additives (other than the ionizable polymer and ionizable surfactants used to prepare the thickener system described below) which increase the viscosity of the solvent phase even in the absence of the thickener system. Certain auxiliary thickeners may act synergistically with the thickener system to increase the viscosity of the resultant formula. Auxiliary thickeners include but are not limited to soluble and swellable polymers and associative colloidal thickeners such as silica, magnesium aluminum silicate, and the like.

"Emollient" as used herein refers broadly to materials which are capable of maintaining or improving the moisture level, compliance, or appearance of the skin when used repeatedly.

"Emulsifier" as used herein refers to molecules comprising hydrophilic (polar) and hydrophobic (non-polar) regions on the same molecule capable of reducing the surface tension of water or the interglacial tension between an immiscible liquid or solid component and the solvent of the composition.

"Emulsion" as used herein refers to a stable dispersion of one liquid in a second immiscible liquid. Emulsion also refers to stable dispersions of a solid in an immiscible liquid wherein the solid was formed by cooling below the freezing point of the solid composition.

"Ionizable Group" as used herein refers to a group capable of forming an ion such as a primary, secondary, or tertiary amine, acids, and permanently charged groups such as those in quaternary amine salts.

"Ionizable Polymer" as used herein refers to a natural, modified-natural, or synthetic molecule having repetitive units and having at least three ionizable groups per molecule.

"Ionizable Surfactant" as used herein refers to molecules comprising hydrophilic (polar) and hydrophobic (non-polar) regions on the same molecule, and has at least one ionizable group per molecule.

"Lotion" means liquid or cream, free of any propellant.

"Melt temperature" ($T_m$) as used herein refers to the temperature at which compositions or emulsions of the present invention dramatically lose viscosity.

"Permanently Charged" as used herein refers to a group that remains charged independent of pH or hydrogen ion concentration, such as a quaternary amine.

"Solvent," "solvent system," or "hydroalcoholic solvent" as used herein refer to the alcohol and water combination in the present invention.

"Stable" as used herein refers to a composition that displays less than or equal to 10% by volume separation after centrifuging at 1545×g for 30 minutes at ambient temperature.

"Thickener System" as used herein refers to a complex of at least one charged polymer and at least one oppositely charged emulsifier.

DETAILED DESCRIPTION OF THE INVENTION

The invention provides a composition comprised of a lower chain alcohol, water, and a thickening system. The thickening system includes a complex of a charged polymer and an oppositely charged surfactant. This complex is formed as a result of reaction between ionizable groups on both the polymer and the surfactant to form ionic groups on both, which then ionically associate. Preferably, this complex is formed as a result of acid-base reactions of the ionizable groups on the polymer and the surfactant. For example, the polymer can have acidic or basic groups that, when combined with a surfactant having acidic or basic groups neutralize each other, thereby forming charged species. These charged species then ionically associate to form a complex that comprises the thickening system in the hydroalcoholic compositions of the present invention. The charged surfactant molecules can also hydrophobically associate as a result of the hydrophobic regions of the surfactant.

Although the ionizable polymers and surfactants used to prepare the thickening system of the present invention may be capable of thickening (i.e., increasing the viscosity) a hydroalcoholic solvent system when used alone (i.e., just a polymer or mixture of polymers or just a surfactant or mixture of surfactants), there is significant improvement in the thickening of a hydroalcoholic solvent system (particularly at higher alcohol to water ratios) if the polymers and surfactants are chosen and combined such that they form a complex.

Hydroalcoholic Solvent System

The compositions of the present invention include one or more alcohols in combination with water, thereby producing a hydroalcoholic solvent system. The alcohol used in the compositions of the present invention is a lower chain hydrocarbon alcohol (referred to herein as a "lower alcohol"), particularly a C1–C4 alcohol (i.e., an alcohol having 1–4 carbon atoms). In preferred embodiments, the alcohol is ethanol, 2-propanol (i.e., isopropanol), or n-propanol. In more preferred embodiments, the alcohol is ethanol. Ethanol is a preferred alcohol because it provides quick killing of a broad spectrum of microbes. Furthermore, it has an acceptable odor to health practitioners and patients.

The lower alcohol to water ratio in the compositions of the present invention is at least about 20:80 by weight (i.e., the lower alcohol is present in an amount of at least about 20 weight percent, and the water is present in an amount of about 80 weight percent, based only on the weight of the water plus the lower alcohol within the composition), preferably at least about 35:65, more preferably at least about 40:60, even more preferably at least about 50:50, and most preferably at least about 60:40, by weight. Typically, compositions of the present invention have an alcohol to water ratio of no greater than about 99:1 by weight. Compositions having an alcohol to water ratio within a range of about 40:60 to 95:5 by weight (i.e., 40–95 weight percent alcohol and 5–60 weight percent water, based only on the weight of water plus lower alcohol in the composition) ensure an efficacious immediate bacterial kill. In particular preferred embodiments, the lower alcohol to water ratio is within a range of about 50:50 to about 85:15, more preferably about 60:40 to about 75:25. Higher ratios of alcohol to water are used in preferred embodiments for optimum antimicrobial activity and to ensure the composition is fast drying.

Thickener System

The thickener system useful in this invention affects the cosmetic attributes of the final composition. Preferably, hand preps and lotions of the invention have the following desirable cosmetic attributes. The composition should not result in excessive clumping of glove powder beneath powdered surgical gloves and should not affect the integrity of the glove material. The compositions should preferably maintain an acceptable viscosity (e.g., at least about 4000 centipoise) at ambient temperatures (i.e., 21–25° C.), and preferably up to about 35° C. Preferred compositions are stable to heat and cool cycles (heating up to 50° C. or higher and cooling to ambient temperature) as well as freeze/thaw cycles (cooling to −30° C. and warming to ambient temperature). All of these cosmetic attributes are affected by the types and amounts of polymers and surfactants chosen, which combine to form a complex that comprises the thickener system of the present invention.

The thickener system of the invention is compatible with the hydroalcoholic solvent system described above in order to provide suitable stability, acceptable cosmetic properties, and appropriate viscosity. Compositions of this invention have a viscosity of at least about 4,000 centipoise (cps), preferably at least about 10,000 cps, more preferably at least about 20,000 cps, even more preferably at least about 50,000 cps, and most preferably at least about 80,000 cps (and even as high as about 500,000 cps or more), at 23° C., measured using a very low shear viscometer such as Brookfield LVDV-I+ viscometer and T spindles with a heliopath adapter. Because certain optional ingredients, such as emollients, may affect the viscosity (either positively or negatively), the measured viscosity is that of the final composition, with all of these additional components but without any added auxiliary thickeners (e.g., noncomplexed polymeric thickeners or colloidal thickeners).

The viscosity of the present invention is imparted by a thickener system prepared by combining at least one ionizable polymer and at least one ionizable surfactant. Upon combining these components in a hydroalcoholic solvent, a complex (i.e., ionic association) of a charged polymer and an oppositely charged surfactant is formed. The polymer may be positively or negatively charged once it has been combined with the surfactant. Similarly, the surfactant may be positively or negatively charged once it has been combined with the polymer, as long as it is of the opposite charge to that of the polymer. As used herein, a "complex" refers to the association of ionic polymer and surfactant molecules formed upon ionization of their respective ionizable molecules. Such ionizable molecules may be in the form of acids, bases, or salts, including salts of permanently charged species.

Thus, prior to complexation with the surfactant, the ionizable polymer used to prepare the thickener system is comprised of ionizable groups (at least three per molecule), which may be basic, acidic, anionic, or permanently charged. Similarly, the ionizable surfactant used to prepare the thickener system is comprised of ionizable groups (at least one per molecule), which may be basic, acidic, anionic, or permanently charged. Upon combining the ionizable surfactant and the ionizable polymer, the thickener system so formed is comprised of a polymeric species ionically bound to a surfactant species of opposite charge, which is preferably present in an amount sufficient to ionically associate with at least about 3 mole-% of the ionic groups on the polymer molecules.

Once reacted with the surfactant in the thickener system, the polymer possesses the opposite charge of the surfactant and is thus complexed with the surfactant. The polymer/surfactant complex may be formed by combining acids and bases. Alternatively, it may be formed by combining salts of opposite charge. For example, a polyquatemary amine polymer (a permanently charged cationic salt) could be combined with an anionic salt surfactant in such a way that a salt exchange occurs forming the polymer/surfactant complex. Formation of a polymer/surfactant complex from permanently charged species may be promoted by differential solubility of the polymer/surfactant complex and the low molecular weight secondary salt so formed. For example, combination of poly(trimethylaminoethylacrylate, chloride salt) with a alkyl sulfate, sodium salt would produce a complex of the polymer/surfactant and the secondary salt sodium chloride. If the secondary salt and/or the polymer/surfactant complex have limited solubility in the hydroalcoholic solvent, the equilibrium will favor complex formation.

For surfactants that are acidic in nature (and thus carry a negative charge once neutralized by the polymer), the polymer should be basic, and therefore is comprised of groups that contain basic functionality. For surfactants that are basic in nature (and thus carry a positive charge once neutralized by the polymer) the polymer should be acidic, and therefore is comprised of groups that contain acidic functionality.

Examples of basic groups include primary, secondary, or tertiary amines, which upon neutralization form protonated amino groups. Examples of acidic groups, which upon neutralization form anionic groups, include hydrogen sulfate ($—OSO_2OH$), sulfonic acid ($—SO_2O$), hydrogen phosphate (($—O)_2P(O)OH$ or $—OP(O)(OH)_2$ or $—OP(O)(OH)O^-M^+$), phosphonic acid ($—PO(OH)_2$ or $—PO(OH)O^-M^+$), and carboxylic acid ($-CO_2H$). In these formulae, M is a positively charged counterion and is selected from the group consisting of hydrogen, sodium, potassium, lithium, ammonium, calcium, magnesium or $N^+R'_4$ R' is independently an alkyl group of 1 to 4 carbon atoms optionally substituted with N, O, or S atoms.

The ionizable polymer used to prepare the thickener system in the compositions of the present invention may be a homopolymer or a copolymer and may be of natural, modified natural, or synthetic origin. It is preferably low enough in molecular weight to ensure that the composition does not have a slimy feel during application to the skin as when applying a lotion to the hands. Herein, preferred ionizable polymers are of low enough molecular weight that a hydroalcoholic solvent system in a ratio of 40:60 alcohol to water, containing an ionizable polymer in an amount of 4% by weight, has a viscosity of less than about 50,000 centipoise (cps), preferably less than about 30,000 cps, more preferably less than about 15,000 cps, and most preferably less than about 4000 cps. A slimy feel is usually imparted by higher molecular weight polymers, such as polyethylene oxide, that impart not only a high viscosity to the composition but create a highly viscoelastic composition as well. The viscous compositions of this invention, however, are believed to derive their thickening efficiency from a hydrophobic association of the surfactants which are, in turn, ionically associated with the polymeric chains. These Van der Waals and/or ionic associations are generally easily disrupted making the lotions shear-sensitive and therefore easy to apply because the shear used during application decreases the viscosity significantly. It will be understood by one of skill in the art, however, that a certain amount of viscoelasticity and/or high yield stress may be highly desirable toward imparting stability to the compositions of the present invention.

The ionizable polymer used to prepare the thickener systems of the present invention are preferably basic or acidic. Suitable basic polymers include groups that are primary, secondary, or tertiary amines, or combinations thereof. Examples of suitable polymers with basic functionality include, but are not limited to, polymers based on unsaturated monomers wherein at least one monomer is an unsaturated primary, secondary, or tertiary amine such as polyacrylates based on dialkylaminoalkylacrylate (e.g., dimethylaminoethylacrylate), dialkylaminoalkylmethacrylate (e.g., dimethylaminoethylacrylate), alkyldiallylarnine (e.g., methyldiallylamine), dialkylaminoalkylacrylamide (e.g., dimethylaminopropylacrylamide), dialkylaminoalkylmethacrylamide (e.g., dimethylaminopropyhnethacrylamide). Other suitable polymers with basic functionality include polymers prepared by reaction of suitable reagents that leave free primary, secondary, or tertiary amine groups (e.g., polyvinylalcohol reacted with 2,3-epoxypropylamine), polymers based on aziridine such as aziridine modified polymers as well as polyethyleneimine, and natural polymers such as amino functional polysaccharides (e.g., chitosan and modified chitosan), and aminofunctional proteins and polypeptides (e.g., polylysine). Combinations of these polymers can also be used.

Suitable acidic polymers include acidic functionality such as hydrogen sulfate, sulfonic acid, hydrogen phosphate, phosphonic acid, and carboxylic acid, as listed above. Examples of suitable polymers with acidic functionality include, but are not limited to, polymers based on unsaturated monomers wherein at least one monomer is an unsaturated acid. For example, suitable unsaturated acids include acrylic acid, methacrylic acid, vinyl phosphonic acid, vinyl sulfonic acid, and 2-methyl-2-(1-oxo-2-propenyl)amino-1-propane sulfonic acid (homopolymer is commercially available from Henkel Corp. as "HSP-1180"). Other polymers containing free acid groups are also suitable such as "PECO-SIL PS-100" polymer available from Phoenix Chemical Inc., Somerville, N.J., which is a dimethicone copolyol phosphate, as well as "GANTREZ" ES, SP, and V series polymers available from ISP, Wayne, N.J., which are monoalkyl esters of poly(methyl vinyl ether/maleic acid).

The ionizable polymers used to prepare the thickener system may also include hydrophobic side chains that are capable of hydrophobically associating with the ionizable surfactant and/or other hydrophobic side chains of other polymer molecules. Examples of suitable hydrophobic side chains include alkyl side chains having at least 16 carbon atoms, preferably at least 18 carbon atoms, and more preferably at least 20 carbon atoms, polystyrene side chains (typically of about 2,000 to 30,000 number average molecular weight), and the like, and mixtures thereof.

Suitable surfactants for use in the present invention are comprised of molecules having hydrophilic (polar) and hydrophobic (non-polar) regions on the same molecule and conform to the general structure:

$$(R)_a(L)_b$$

wherein "R" represents a hydrophobic group, "L" represents a hydrophilic group having at least one ionizable group when the surfactant is ionizable (i.e., prior to reaction with the polymer) or at least one ionic group when the surfactant is charged (i.e., as a result of reaction with the polymer), and "a" and "b" are independently 1 to 4. These compounds have at least one ionizable group, which may be acidic, basic, anionic or permanently charged.

In this formula, "R" includes an alkyl group of at least 16 carbon atoms, preferably at least 18 carbon atoms, more preferably at least 20 carbon atoms, and most preferably at least 22 carbon atoms; an alkenyl group of at least 16 carbon atoms, preferably at least 18 carbon atoms, and more preferably 20 carbon atoms; or an aralkyl or aralkenyl group of at least 20 carbon atoms, preferably at least 24 carbon atoms, and more preferably at least 26 carbon atoms. In a preferred embodiment "R" is unbranched. These hydrophobic groups allow for hydrophobic association of the surfactant molecules.

In the above formula, "L" represents a basic group including a primary amine, a secondary amine, or a tertiary amine; an acidic group (protonic acid) including hydrogen sulfate (—OSO$_2$OH), sulfonic acid (—SO$_2$OH), hydrogen phosphate ((—O)$_2$P(O)OH or —OP(O)(OH)$_2$ or —OP(O)(OH)O$^-$M$^+$), phosphonic acid (—PO(OH)$_2$ or —PO(OH)O$^-$M$^+$), and carboxylic acid (-CO$_2$H), wherein, M is a positively charged counterion and is selected from the group consisting of hydrogen, sodium, potassium, lithium, ammonium, calcium, magnesium or N$^+$R'$_4$ where each R' is independently an alkyl group of 1 to 4 carbon atoms optionally substituted with N, O, or S atoms; an anionic group derived from an acidic group or salt of an acidic group; or a permanently charged group such as a quaternary amine.

The surfactant may have more than one acidic, basic, anionic, or permanently charged hydrophilic group. It may also have additional nonionic groups, such as amide, ester, alcohol, sorbitan, polyglyceryl (generally having 2 to 10 or more glyceryl units), polyglucoside (generally having 1 to 10 or more glucoside units), polyethylene glycol (generally having 1 to 100, preferably 5 to 50 polyethylene oxide units), or combinations thereof Examples of suitable surfactants are listed in greater detail below. The surfactant is typically used in an amount effective to complex with (for example, by neutralization) at least about 3 mole-% of the ionizable polymer groups. Preferably, the surfactant is used in an amount effective to complex with (for example, by neutralization) at least about 5 mole-%, more preferably at least about 10 mole-%, most preferably at least about 20 mole-%, and even as high as 100 mole-% or more (e.g., 200 mole-%), of the ionizable polymer groups. In this way, the surfactant is present in its charged form in the thickener system in an amount sufficient to ionically associate with at least about 3 mole-% (preferably at least about 5 mole-%, more preferably at least about 10 mole-%, most preferably at least about 20 mole-%, etc.) of the ionic groups on the polymer molecules. In certain systems, excess surfactant (on a molar basis) may be desirable.

The thickener system can be prepared from one or more ionizable polymers and one or more ionizable surfactants. Each of these may be chosen from a single class of compounds or from more than one class. If more than one surfactant is used, it is preferably present in a concentration of at least about 0.05% by weight, and more preferably at least 0.1% by weight, based on the total weight of the composition. Thickener systems of the present invention are capable of achieving high viscosities at relatively low total surfactant concentrations. The total concentration of surfactants present in the thickener system is generally less than about 8% by weight, preferably less than about 5% by weight, more preferably less than 4% by weight, and most preferably less than 3% by weight of the total composition of the present invention.

As used herein, a surfactant is considered part of the thickener system if it is charged, has an opposite charge to that of the charged polymer, is capable of associating with the charged polymer, and its presence in the composition results in an increase in the viscosity of the composition. Certain surfactants or emulsifiers that do not have these characteristics (e.g., non-ionic surfactants or emulsifiers) may also be present in the composition and may actually increase the viscosity of the composition, but for purposes of this invention, they are not considered part of the thickener system. For example, if a certain surfactant does not result in increasing the viscosity of the composition, it is considered an emollient or stabilizer, for example, which are defined below.

In preferred embodiments, at least one of the surfactants is a solid at ambient temperature. Such solid surfactants typically include at least one long chain hydrocarbon of at least 16 carbon atoms, preferably at least 18 carbon atoms, and more preferably at least 22 carbon atoms. For systems having a lower alcohol to water ratio in excess of about 50:50, the long chain hydrocarbon group preferably has at least 18 carbon atoms. The longer hydrocarbon chain length is believed to reduce the irritation potential of the compositions.

Many commercially available surfactants (also often referred to as emulsifiers) are actually comprised of a mixture of chain lengths. For example, the surfactant behenic acid as commercially supplied is actually a mixture of acids consisting of primarily C22, C20, and C18 fractions but contain detectable levels of C24 and C16 fractions. For this reason, unless otherwise specified (as above) the chain lengths specified herein refer to the number average chain length.

Preferably, the ionizable polymers and surfactants are selected such that the composition, free of auxiliary thickeners, has a viscosity of at least about 4,000 centipoise at 23° C. Also, the ionizable polymers and surfactants are selected such that the composition has a viscosity that is greater than the same composition without either the ionizable polymer or the ionizable surfactant. That is, each of the polymer and the surfactant alone may be capable of increasing the viscosity of the composition. However, when used together, the complex of the charged polymer and charged surfactant is capable of increasing the viscosity of the composition to a much greater extent than either the ionizable polymer or the ionizable surfactant alone.

The amount of ionizable polymer in the thickener system is preferably less than about 12% by weight, more preferably less than about 8% by weight, and most preferably less than about 4% by weight of the total composition of the present invention. The amount of the thickener system (i.e., polymer/surfactant complex) is preferably less than about 12% by weight, more preferably less than about 10% by weight, even more preferably less than or equal to about 8% by weight, and most preferably less than or equal to about 6% by weight.

Preferred compositions of the present invention, which are substantially free of auxiliary polymeric thickening agents, have a "melt temperature" ($T_m$). If compositions are heated above this melt temperature, they dramatically lose (i.e., decrease) viscosity. The compositions of the present invention preferably have melt temperatures greater than about 25° C. in order to maintain a high viscosity (e.g., at least about 4000 centipoise) at ambient temperatures (i.e., 21–25° C.). In certain compositions, the melt temperature is greater than about 35° C. in order to generally maintain a high viscosity (e.g., at least about 4000 centipoise) once applied to the skin. Some preferred compositions have a melt temperature greater than about 40° C. in order to allow shipping and handling without refrigeration.

Thickener systems affect the melt temperature of a given composition. For example, in order to obtain a melt temperature in excess of about 25° C. (and preferably, about 35° C.), the thickener system includes at least one surfactant which is solid (e.g., a wax) at ambient temperature. Preferably, all the surfactants of the thickener system are solid at ambient temperature to increase the melt temperature of the resultant composition.

Also, the structure of surfactants in a thickener system affects the melt temperature of the resultant composition. In preferred embodiments, at least one surfactant in a thickener system is capable of promoting a crystalline structure. Crystallinity is promoted by long straight chain alkyl groups. Therefore, at least one surfactant preferably comprises a saturated straight chain hydrocarbon of at least 16, preferably at least 18, and more preferably at least 20 carbon atoms.

In addition to effecting the melt temperature of a composition, the surfactant chain length also helps to determine the maximum level of lower alcohol that can be used in the composition while maintaining a viscous composition (if so desired) and the concentration of surfactants required in the thickener system. For example, at higher levels of lower alcohol, longer chain surfactants are desired to produce stable viscous emulsions. It is believed that higher levels of lower alcohol tend to swell or solubilize the surfactants to a greater degree than lower levels of the same alcohol. Therefore, as the concentration of the lower alcohol increases, the chain length of the hydrocarbon group in the surfactants of the thickener system also increases in order to maintain a melt temperature over 25° C. (preferably, over 35° C.). In addition, as the chain length of the hydrophobic component in the thickener system increases, the amount of surfactant required to achieve a certain viscosity decreases.

That is, the amount of lower alcohol in the hydroalcoholic system can affect the choice of surfactant, and vice versa. For example, if the composition includes a lower alcohol to water ratio in excess of about 50:50, the thickener system should include at least one surfactant having a number average chain length of at least 16 carbon atoms. If the composition includes a lower alcohol to water ratio in excess of about 60:40, the thickener system should include at least one surfactant having a number average chain length of at least 18 carbon atoms. If the composition includes a lower alcohol to water ratio in excess of about 64:36, the thickener system should include at least one surfactant having a number average chain length of at least 20 carbon atoms.

Preferred thickener systems used in the compositions of the present invention are capable of producing viscoelastic compositions that are preferably very stable. By varying the ratio of surfactant and polymer, the degree of elasticity can be adjusted from almost a purely viscous composition to a highly elastic and even gel-like composition. If emollients are added, increasing the elasticity of the system imparts added stability to prevent separation of immiscible emollients. Excessive elasticity, however, is not preferred because an elastic composition usually does not provide a cosmetically appealing product. Addition of certain surfactants with at least two hydrophobic groups may limit the viscoelasticity while ensuring viscous stable compositions. A favored class of surfactants having multiple hydrophobic groups are tertiary amines conforming substantially to the following structure:

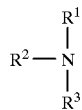

wherein: $R^1$ and $R^2$ are long chain alkyl or alkenyl hydrocarbon groups of at least 16 carbon atoms; $R^3$ is a short chain alkyl group of 1 to 4 carbon atoms, preferably methyl or ethyl. Some preferred structures include distearylmethylamine and dibehenylmethylamine. Dialkyl (optionally ethoxylated) phosphates may also be useful in limiting the amount of viscoelasticity.

Other suitable multiple hydrophobic surfactants which may be added in addition include dialkylglycerol esters, trialklglycerol esters, polyglycerol alkyl esters, ethylene glycol dialkylesters, polyethylene glycol dialkylesters, dialkylamides of diamines such as ethylene diamine, polyalkylesters of pentaerythritol, and alkyl esters of polyethyoxylated alkyl alcohols.

The following surfactant classes are offered as nonlimiting examples of suitable surfactants for use in the present invention. Examples of some preferred surfactants are provided for each class.

Class 1: Tertiary Amines (Basic Compounds)

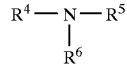

wherein $R^4$ is a straight chain alkyl or alkenyl group of at least 14 carbon atoms, preferably at least 16 carbon atoms, more preferably at least 18 carbon atoms, and most preferably at least 20 carbon atoms, optionally substituted by N, O, and S atoms, or an aralkyl or aralkenyl group of at least 16 carbon atoms, preferably at least 18 carbon atoms, and more preferably at least 22 carbon atoms, optionally substituted by N, O, and S atoms. $R^4$ may also be selected from polyethoxylated or polypropoxylated alkyl or alkenyl alcohol chains having 1–50 moles of ethylene oxide or propylene oxide groups per mole of surfactant. $R^5$ is a short chain alkyl group of 1 to 4 carbon atoms, preferably methyl, ethyl, or propyl; and $R^6$ is the same as $R^4$ or $R^5$.

Some examples of this class of tertiary amines useful in preparing a thickener system of the invention include, but are not limited to, behenamidopropyldimethylamine available as Incromine BB from Croda, Inc. of Parsippany, N.J.; tallowdimethylamine; dihydrogenated tallow methyl amine; stearyl diethanolamine; polyethoxylated tallow diethanolamine available as "EHOMEEN T" series from Akzo Chemicals Inc. of Chicago, Ill.

Class 2: Alkyl and Alkenyl Primary and Secondary Amines (Basic Compounds)

wherein $R^4$ and $R^5$ are as defined above for tertiary amines (Class 1). Some examples of surfactants from these classes of amines useful in a thickener system of the invention include, but are not limited to, tallowamine available as "ARMEEN T" and ditallow amine available as "ARMEEN 2T", both of which are available from Akzo Chemicals Inc.

Classes 3 and 4: Acidic (M=H) or Anionic Surfactants

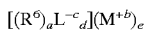

wherein $R^6$ is an alkyl, alkenyl, or aralkyl group of at least 14 carbon atoms, preferably at least 16 carbon atoms, more preferably at least 18 carbon atoms, and most preferably at least 20 carbon atoms, optionally comprising oxygen, nitrogen, or sulfur atoms within or substituted upon the alkyl or alkenyl chain; or a polyethoxylated and/or polypropoxylated alkyl, alkenyl group, or aralkyl group, which alkyl, alkenyl, or aralkyl group comprises at least 14 carbon atoms, preferably at least 16 carbon atoms, more preferably at least 18 carbon atoms, and most preferably at least 20 carbon atoms, optionally comprising oxygen, nitrogen, or sulfur atoms within or substituted upon the alkyl, alkenyl, or aralkyl chain. When $R^6$ is a polyethoxylated or polypropoxylated substituent or a copolymeric substituent of ethylene oxide and propylene oxide, these subunits are present in amounts of 1 to 100 moles, preferably 1 to 20 moles per mole of hydrophobe; L is sulfate (—OSO 2O⁻), sulfonate (—SO$_2$O⁻), phosphate ((—O)$_2$P(O)O⁻ or —OP(O)(O⁻)$_2$), or carboxylate (-CO$^{2-}$); M is hydrogen (H⁺), sodium (Na⁺), potassium (K⁺), lithium (Li⁺), ammonium (NH$_4$⁺), calcium (Ca$^{+2}$), magnesium (Mg$^{+2}$), or R"A⁺, wherein R" is hydrogen or an alkyl or cycloalkyl group of about 1 to 10 carbon atoms, and A⁺ is selected from the group of —N⁺(R)$_3$ (e.g., R"A⁺ can be N⁺(CH$_3$R)$_4$, HN⁺(CH$_2$CH$_2$OH)$_3$, H$_2$N⁺(CH$_2$CH$_2$OH)$_2$), or a heterocyclic —N⁺B wherein B comprises 3 to 7 atoms selected from the group of carbon, nitrogen, sulfur and oxygen atoms which complete the nitrogen-containing heterocyclic ring and satisfy the valence on the nitrogen atom; and wherein R is the same as R" and may also be substituted in available positions with oxygen, nitrogen or sulfur atoms; "a" and "c" are independently 1 or 2; "b" and "d" are independently 1, 2 or 3; and "e" is equal to (c times d)/b.

Nonlimiting examples of preferred surfactants from this acidic class (when M=H) or anionic class (when M=sodium, potassium, lithium, etc.) suitable for use in a thickener system of the invention include behenic acid available as "CROACID B" from Croda, Inc. and stearyl phosphate available as "SIPPOSTAT 0018" from Specialty Industrial Products, Inc. of Spartanburg, S.C.

Class 5. Quaternary Amine (Permanently Charged) Salts

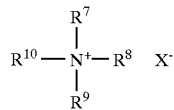

wherein $R^{10}$ is a straight chain alkyl or alkenyl group of at least 12 carbon atoms, preferably at least 16 carbon atoms, more preferably at least 18 carbon atoms, and most preferably at least 20 carbon atoms, or an aralkyl or aralkenyl group of at least 14 carbon atoms, preferably at least 18 carbon atoms, and more preferably at least 22 carbon atoms;

$R^7$ is a short chain alkyl group of 1 to 4 carbon atoms, preferably methyl or ethyl; $R^8$ is the same as $R^7$, or is a long chain alkyl or alkenyl hydrocarbon chain of at least 12 carbon atoms, preferably at least 16 carbon atoms, more preferably at least 18 carbon atoms, and most preferably at least 20 carbon atoms, optionally substituted in available positions by N, O, or S atoms, or $R^8$ is an aralkyl or aralkenyl group of at least 14 carbon atoms, preferably at least 18 carbon atoms, and more preferably at least 22 carbon atoms; $R^9$ is equivalent to either $R^7$ or $R^8$ and is preferably equivalent to $R^8$; and X is a halogen, $R^{11}SO_3$—, $R^{11}SO_4$—, $R^{11}CO_2$—, $(R^{11})_2PO_4$—, or $(R^{11})PO_4$=(wherein $R^{11}$ short chain alkyl group of 1 to 4 carbon atoms, preferably methyl or ethyl).

Nonlimiting examples of quaternary amine surfactants include dibenhenyldimethylammonium methosulfate available as "INCROQUAT DBM-90" from Croda; behenyltrimethylammonium chloride available as "NIKKOL CA-2580" from Barnet Products; and tallowtrimethylammonium chloride available as "ARQUAD T-27W" from Akzo Chemicals, Inc. of Chicago, Ill.

Nonlimiting Examples of Suitable Thickener Systems:

| System No. | Surfactant/(Class) | Polymer/(Class) |
|---|---|---|
| 1 | tertiary amine (base) | polyhydrogen phosphate/acid |
| 2 | tertiary amine (base) | polysulfonic acid/acid |
| 3 | tertiary amine (base) | polycarboxylic acid/acid |
| 4 | hydrogenphosphate/(acid) | polyamine (base) |
| 5 | hydrogen sulfate/(acid) | polyamine (base) |
| 6 | carboxylic acid/(acid) | polyamine (base) |
| 7 | quaternary amine/(permanently charged) | anionic |
| 8 | anionic | quaternary amine/(permanently charged) |

It is a simple matter to test certain combinations of surfactants and polymers to determine if they provide a suitable thickener system. Screening methodology is set forth in the Examples.

Surfactants other than those required in the composition to provide a thickener system may also function as emollients or stabilizers. For example, certain emollients are also comprised of hydrophobic and hydrophilic regions and are useful in the present invention since they are believed to associate with the surfactant of the thickener system. These emollients tend to affect the stability of the composition. Furthermore, certain dimethicone copolyol surfactants can actually improve the stability of formulations incorporating emollients.

Optional Ingredients and Applications

In addition to alcohol, water and the thickener system, the compositions of the present invention may optionally include ingredients such as salts, emollients, stabilizers, antimicrobials, fragrances, pharmaceutical agents, penatrant enhancers, propellants, and emulsifiers. Each of these optional ingredients along with the effect each has upon the properties of the final composition is discussed below.

Salts

The melt temperature and stability of the compositions of the present invention may be affected by adding salts. As the concentration of salt is increased, the ratio of surfactant to polymer may need to change in order to maintain a stable composition. It is important to choose salts which do not create an unstable system and are compatible with any antimicrobials or pharmaceutical agents present in the system. For example, chlorhexidine digluconate (CHG) will precipitate rapidly in the presence of halide salts above a concentration of about 0.1M. Therefore, if a system includes CHG, preferably gluconate salts such as triethanolamine gluconate or sodium gluconate, are used.

Because many compounds are pH dependent, it may also be beneficial to incorporate pH buffers to maintain the desired pH during storage and use, thereby providing long term stability. The choice of the preferred pH buffer would depend on the thickener system. Suitable buffers are those that do not interfere with the complexation of the polymer/surfactant complex.

Stabilizers

A stable composition is one which does not separate more than 10% by volume after centrifuging at 1545×g for 30 minutes as measured at the longitudinal midpoint of the sample tube. It is also recognized that stability may be time dependent due to precipitation of the polymer/surfactant complex, crystallization of emulsifiers and/or emollients present in the system, coalescence of emollients, emulsifiers and the like. Therefore, preferred compositions do not exhibit separation of more than 10% after standing for 6 months at ambient conditions. Two types of stabilizers are useful in the present invention. These include (1) those stabilizers that complex with emulsifier or surfactant hydrophilic head groups, and (2) those that associate with the emulsifier or surfactant hydrophobic tails. Certain stabilizers may perform both functions. For example, polymers, surfactants or emulsifiers comprising 1,2-diol-containing head groups such as alkylpolyglucosides, monoalkylglycerides, and polyglycerol alkyl esters, may be "stabilized" by adding borate ion. Without intending to be bound by theory, it is believed that borate ions complex with adjacent head groups which may increase the association of hydrophobic tails by holding them in close proximity.

Natural, modified-natural, or synthetic polymers comprised of pendent long chain alkyl groups (greater than 12 and preferably greater than 16 carbon atoms) such as stearyl modified cellulose derivatives, stearyl modified proteins such as wheat protein, stearyl modified collagen, polymers comprising stearyl methacrylate, and the like, are capable of stabilizing compositions of the present invention. Such added components may also increase the melt temperature of compositions of the present invention. It is believed that the pendent alkyl groups in these polymers associate by Van der Waals interactions with the hydrophobes of a thickening system, thereby enhancing the stability of the crystalline structure. Polymeric thickeners which do not have associative pendent alkyl chains may also increase the melt temperature presumably by increasing the viscosity of the continuous phase. A nonlimiting example of such thickeners are quaternary celluloses such as "CELQUAT 230M" available from National Starch of Bridgewater, N.J. In a preferred embodiment stearyldimonium hydroxypropyl cellulose commercially available as "CRODACEL QS" from Croda Inc., Parsippany, N.J. is added as a stabilizer.

Emollients

Emollients are typically added to hand lotions or hand preps because they act to increase the moisture content of the stratum comeum. Emollients are generally separated into two broad classes based on their function. The first class of emollients function by forming an occlusive barrier to prevent water evaporation from the stratum comeum. The second class of emollients penetrate into the stratum comeum and physically bind water to prevent evaporation. The first class of emollients is subdivided into compounds that are waxes at room temperature and compounds which are liquid oils. The second class of emollients includes those that are water soluble and are often referred to as humectants.

For the purposes of this invention, the thickener system is considered separate and distinct from any emollients which may be added even though it is recognized that the surfactant may function as an occlusive emollient and aid in maintaining or improving the skin condition. It is also recognized that the polymer/surfactant system may function to improve skin condition either as an occlusive complex, or by binding water, or both. If emollients are included, they preferably comprise about 0.5% to about 30%, more preferably about 2% to about 20%, and most preferably about 4% to about 16%, by weight of the formulation.

The ratio of wax to liquid emollients (oils and humectants) in a preferred embodiment of the invention is within a range of about 5:1 to about 1:5 and preferably about 1:3 to about 3:1. Emollients may be selected from any of the classes known in the art. A general list of useful emollients appears in U.S. Pat. No. 4,478,853 (Chaussee), EPO Patent Publication No. 0 522 624 A1 (Dunphy et al.) and in the *CTFA Cosmetic Ingredient Handbook* published by The Cosmetic, Toiletry, and Fragrance Association, Wash. D.C. (1992) under the listings "Skin Conditioning agents," "emollients," "humectants," "miscellaneous," and "occlusive."

In preferred embodiments, emollients are chosen from the following nonlimiting list of general emollients, occlusive emollients and humectants. Examples of general emollients include short chain alkyl or aryl esters (C1–C6) of long chain straight or branched chain alkyl or alkenyl alcohols or acids (C8–C36) and their polyethoxylated derivatives; short chain alkyl or aryl esters (C1–C6) of C4–C12 diacids or diols optionally substituted in available positions by —OH; alkyl or aryl C1–C9 esters of glycerol, pentaerythritol, ethylene glycol, propylene glycol, as well as polyethoxylated derivatives of these and polyethylene glycol; C12–C22 alkyl esters or ethers of polypropylene glycol; C12–C22 alkyl esters or ethers of polypropylene glycol/polyethylene glycol copolymer; and polyether polysiloxane copolymers. Additional examples of occlusive emollients include cyclic dimethicones, polydialkylsiloxanes, polyaryl/alkylsiloxanes, long chain (C8–C36) alkyl and alkenyl esters of long straight or branched chain alkyl or alkenyl alcohols or acids; long chain (C8–C36) alkyl and alkenyl amides of long straight or branched chain (C8–C36) alkyl or alkenyl amines or acids; hydrocarbons including straight and branched chain alkanes and alkenes such as squalene, squalane, and mineral oil; polysiloxane polyalkylene copolymers, dialkoxy dimethyl polysiloxanes, short chain alkyl or aryl esters (C1–C6) of C12–C22 diacids or diols optionally substituted in available positions by OH; and C12–C22 alkyl and alkenyl alcohols. Nonlimiting examples of preferred humectant type emollients include glycerol, propylene glycol, dipropylene glycol, polypropylene glycol, polyethylene glycol, sorbitol, pantothenol, gluconic acid salts and the like.

Although a thickener system is responsible for the stability and overall consistency of compositions of the present invention, emollients may also affect the viscosity, stability, and melt temperature of a composition. It is anticipated that a single emollient may be added to the present invention or two or more emollients may be added to the composition. A wide range of emollients may be added to the formulations of the present invention. Preferably wax and oil type emollients along with water soluble emollients are used. In a preferred embodiment, emollient systems are comprised of humectants in addition to occlusive wax and oil emollients in concentrations which achieve a moisturizing but not greasy composition which maintains and improves the condition of the skin upon repeated use. Ideally, emollients are non-comedogenic and are chosen to ensure no skin irritation or sensitization reaction occurs. This is particularly critical since the composition of the present invention will likely be worn in an occluded condition under surgical gloves. Furthermore, emollients should be chosen which do not affect the integrity of the glove material. For example, since hydrocarbon emollients such as mineral oil and petrolatum can detrimentally affect the tear strength of surgical gloves, these emollients may need to be avoided for compositions employed as presurgical disinfectants.

Without being bound or limited by theory, it is believed that if emollients are added to the present compositions, they may be present in four distinct regions. The emollients could occur (1) as a soluble species in the solvent phase, (2) dispersed as emulsified droplets within the composition, (3) incorporated into an emulsifier micelle or network if present, or (4) as a separate and distinct emulsion. As earlier stated, emollients can affect the melt temperature of a composition. Those emollients that are soluble or dispersible in the solvent phase tend to have little or no affect on the melt temperature and are therefore preferred. These emollients include the humectant and general emollients. The most preferred general emollients are those which are essentially insoluble in water but soluble in the hydroalcoholic solvent. These emollients are also preferred since they remain soluble and uniformly dispersed even above the melt temperature so that upon cooling to room temperature a uniform composition results. In addition, they are also believed to have little effect on surgical gloves. Such general emollients typically do not have alkyl or alkenyl chains greater than about 14, preferably not greater than 12 and most preferably not greater than about 9 carbon atoms.

Those emollients that are insoluble in the hydroalcoholic solvent may associate with the surfactants of the thickener system and/or additional emulsifiers and may become incorporated into the micelle or crystalline gel network if present. Preferred emollients within this class are those emollients that are very hydrophobic since they tend to maintain a high melt temperature. Those emollients which are capable of associating with and disrupting the emulsifiers of the thickener system tend to decrease the melt temperature and may influence the stability of the composition.

The following are nonlimiting examples of emulsifier/emollient components which improve thickening/stability of compositions of the present invention.

a. Certain wax emulsifiers/emollients have been found to be particularly useful and include solid waxy esters such as: Myristyl Myristate, Cetyl Palmitate, Myristyl Stearate, Stearyl Behenate, Behenyl Isostearate, Isostearyl Behenate, Behenyl Behenate, Lauryl Behenate, Behenyl Erucate. These have the following formula: $R^{12}$—$CO_2$—$R^{13}$ wherein $R^{12}$ is an alkyl or alkenyl group of at least 14 carbon atoms, and $R^{13}$ is an alkyl or alkenyl group of at least 4 carbon atoms.

b. Long chain hydrocarbon di-esters or tri-esters of polyhydric alcohols with a melting point of greater than 23° C., including solid esters such as glycerol tribehenate and sorbitan tristearate.

c. Pure lanolins and lanolin derivatives (e.g., hydrogenated lanolin), which provide excellent emolliency but can also improve the stability of the emulsion when used in combination with oil emollients.

d. Petrolatums, which are mixtures of oily and waxy long chain hydrocarbons, provide excellent emolliency, and can also improve the stability of the emulsion when used in combination with oil emollients.

e. Microcrystalline waxes and branched hydrocarbon waxes with a melting point of greater than 50° C. and a molecular weight of greater than 400. Examples of this includes, but is not limited to, "VYBAR 103" branched hydrocarbon with a number average molecular weight of 2800, and "ULTRAFLEX" microcrystalline wax, both of which are available from Petrolite Corp. of Tulsa, Okla.

f. Oxidized waxes and modified hydrocarbon waxes, which are prepared from waxes modified by oxidation, salts of oxidized waxes, maleic anhydride adducts of polyolefins and urethane derivatives of oxidized synthetic or petroleum waxes. Applicable waxes could include Petrolite's Cardis or Petronauba microcrystalline and polyethylene-based oxidized products, Polymekon (salts) and Ceramer (anhydride adducts).

g. Fully saturated homopolymers of polyethylene, or copolymers of various alkene monomers having a molecular weight at or below 3,000 with a melting point below 130° C. and low melt viscosities. Applicable waxes could include "POLYWAX" available from Petrolite Corp.

Fragrances

The compositions of the present invention may also comprise a fragrance. If fragrances are included the fragrances must be chosen carefully since some fragrances are known to cause skin irritation and/or sensitization reactions.

Antimicrobials

In addition to the lower alcohols present in the composition of the present invention, other antimicrobials (i.e., a secondary antimicrobial agent) may be added to enhance the antimicrobial action of the compositions of the present invention. This may be particularly desirable in critical uses such as presurgical hand scrubs. Suitable additional antimicrobials include iodine and its complexed forms such as povidone/iodine, chlorhexidine salts such as chlorhexidine digluconate (CHG), parachlorometaxylenol (PCMX), hexachlorophene, phenols, surfactants comprising a long chain hydrophobe (C12–C22) and a quaternary group, triclosan, "LAURICIDIN" glyceryl monolaurate, quaternary silanes, hydrogen peroxide, phenols, silver, silver salts such as silver chloride, silver oxide and silver sulfadiazine and the like. In order to reduce chances for irritation and yet maintain efficacy, the antimicrobial level should be adjusted to the minimum level which maintains a low bacteriological count for 6 and most preferably for 12 hours after application.

The most preferred additional antimicrobial is chlorhexidine since it is capable of ensuring long term antimicrobial efficacy. If chlorhexidine is added to the present invention it is preferably present as a soluble salt. The diacetate and digluconate salts are preferred. The most preferred antimicrobial is chlorhexidine digluconate (CHG). CHG is preferably present at a concentration of about 0.05–5.0%, more preferably about 0.1–3%, even more preferably about 0.25–2%, and most preferably about 0.5–1%, by weight, based on the total weight of the composition. Chlorhexidine is a bis(diguanide) and therefore is very basic and is capable of forming multiple ionic bonds with anionic materials. For this reason, chlorhexidine-containing thickener system are preferably based on non-precipitating surfactants and polymers. These include certain alkyl phosphate and alkyl sarcosinate surfactants in combination with aminofunctional polymers. In addition, certain zwitterionic and cationic non-precipitating surfactants may also be useful.

Propellants

The compositions of the present invention may also be formulated into an aerosol foam or mousse by addition of an appropriate propellant. The propellant must be chosen to ensure proper delivery from the container to prevent clogging of the valve. The propellant can be chosen from chiorofluorocarbons (CFCs), hydrochlorofluorocarbons (HCFCs), hydrofluorocarbons (HFCs), perfluorinated alkanes, and lower alkanes (C1–C5) as well as nitrous oxide, dimethyl ether, and other solvent-soluble propellants. Preferred propellants are lower alkanes such as propane, butane, and isobutane since these result in a dramatic loss in viscosity making the formulation easy to dispense. A 70:30 mixture of propane/isobutane is a particularly preferred embodiment. In order to produce an aerosol composition the antimicrobial lotion is first formulated and charged into an appropriate pressure rated container. If convenient, the formulation may be heated above the melt temperature in order to facilitate filling. The propellant is then added under pressure at approximately 2–30% preferably 3–20% by volume. The propellant may form a separate layer or may remain emulsified in the composition.

Pharmaceutical Agents

Pharmaceutical agents (e.g., medicaments, drugs, prodrugs, etc.) suitable for use in compositions of the present invention are compounds that are intended to be delivered transdermally (i.e., into the skin and/or through the skin into the circulatory system) to a mammal to alter biological function to treat, cure, and/or prevent disease or abnormal conditions.

Suitable pharmaceutical agents exhibit an optimal combination of such properties as water solubility, polarity, structure, and molecular weight. For instance, molecular weights are typically between about 100 daltons and about 5000 daltons, and preferably between about 200 daltons and about 1200 daltons. Examples of suitable pharmaceutical agents include those described in U.S. Pat. No. 4,752,612 (Saito et al.).

Suitable pharmaceutical agents include antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g. nystatin); vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors (e.g., A64077), and angiotensin converting enzyme inhibitors (e.g., captopril, lisinopril); other antihypertensives (e.g., propranolol); leukotriene antagonists (e.g., ICI204,219) antiulceratives such as H2 antagonists; steroidal hormones (e.g., progesterone, testosterone, estradiol, levonorgestrel); antivirals and/or immunomodulators (e.g., 1-isobutyl-1H-imidazo[4,5-c]quinolin-4amine, 1-(2-hydroxyl-2-methylpropyl)-1H-imidazo[4,5-c]quinoline-4-amine, acyclovir); local anesthetics (e.g., benzocaine, propofol); cardiotonics (e.g., digitalis, digoxin); antitussives (e.g., codeine, dextromethorphan); antihistamines (e.g., diphenhydranmne, chlorpheniramine, terfenadine); narcotic analgesics (e.g., morphine, fentanyl); peptide hormones (e.g., human or animal growth hormones LHRH); cardioactive products such as atriopeptides; proteinaceous products (e.g., insulin); enzymes (e.g., anti-plague enzymes, lysozyme, dextranase), antinauseants (e.g., scopolamine); anticonvulsants (e.g., carbamazepine); immunosuppressives (e.g., cyclosporine); psychotherapeutics (e.g., diazepam); sedatives (e.g., phenobarbital); anticoagulants (e.g., heparin); analgesics (e.g., acetamninophen); antimigraine agents (e.g., ergotamine, melatonin, sumatriptan); antiarrhythmic agents(e.g., flecainide); antiemetics (e.g., metoclopramide, ondansetron); anticancer agents (e.g., methotrexate); neurologic agents such as anxiolytic drugs; hemostatics; antiobesity agents; nicotine; and the like, as well as pharmaceutically acceptable salts and esters thereof The pharmaceutical agent is present in a transdermal delivery device of the invention in a therapeutically effective amount, i.e., an amount effective to bring about a desired therapeutic result in the treatment of a condition. The amount that constitutes a therapeutically effective amount varies according to the particular pharmaceutical agent incorporated in the device, the condition being treated, any pharmaceutical agent being coadministered with the selected pharmaceutical agent desired duration of treatment, the surface area of the skin over which the device is to be placed, the type of device being utilized, the choice of excipients, and other components of the device.

Penetration Enhancers

Additional compounds other than the lower alcohol or components of the emulsifier system may also be present in the composition to further boost the penetration of a particular pharmaceutical agent. These penetration enhancers may be present primarily in either the oil-like phase of the emulsion or the hydroalcoholic phase. Non-limiting examples of additional penetration enhancers include $C_8$–$C_{22}$ fatty acids such as isostearic acid, octanoic acid, and oleic acid; $C_8$–$C_{22}$ fatty alcohols such as oleyl alcohol and lauryl alcohol; lower alkyl esters of $C_8$–$C_{22}$ fatty acids such as ethyl oleate, isopropyl myristate, butyl stearate, and methyl laurate; di (lower) alkyl esters of $C_6$–$C_8$ diacids such as diisopropyl adipate; monoglycerides of $C_8$–$C_{22}$ fatty acids such as glyceryl monolaurate; tetrahydroftifryl alcohol polyethylene glycol ether; polyethylene glycol, propylene glycol; 2-(2-ethoxyethoxy)ethanol; diethylene glycol monomethyl ether; alkylaryl ethers of polyethylene oxide; polyethylene oxide monomethyl ethers; polyethylene oxide dimethyl ethers; dimethyl sulfoxide; glycerol; ethyl acetate; acetoacetic ester; N-alkylpyrrolidone; and terpenes. Certain emulsifier systems may also significantly increase the flux of particular pharmaceutical agents. This may be particularly true of emulsifiers that are in a pure state liquids at skin temperature such as those having shorter chain hydrophobes (e.g., methyl laurate), unsaturated hydrophobes (methyl oleate, oleic acid, oleyl alcohol, glycerol monooleate), and branched hydrophobic hydrocarbon chains (isostearyl alcohol).

Transdermal Delivery Systems

The compositions of the present invention can be used in a variety of transdermal delivery systems (e.g., devices). A variety of such systems have been described. The simplest is a lotion of a pharmaceutical agent in the composition of the present invention. Others include matrix devices in which a pharmaceutical agent is incorporated into the composition of the present invention and placed within a polymeric material such as a hydrogel layer or adhesive; reservoir devices in which the pharmaceutical agent-containing hydroalcoholic composition is delivered to the skin through a rate-controlling membrane; drug-in-adhesive devices in which the pharmaceutical agent is placed within the composition of the present invention as part of an adhesive composition; and more complex multilaminate devices involving several distinct layers (e.g., layers for containing the pharmaceutical agent, for containing excipients, for controlling the rate of release of the pharmaceutical agent and excipients, and for attaching the device to the skin). Each of these devices include an adhesive to maintain contact with the patient's skin and a backing that protects the device from external factors while in use, thereby forming a patch.

An exemplary reservoir device comprises a backing, a matrix containing the composition of the present invention with the pharmaceutical agent therein, optionally a membrane for controlling the rate at which the pharmaceutical agent is delivered to the skin, an adhesive layer, and a release liner.

Alternative Applications for the Compositions

The compositions of this invention may be compounded with UV absorbers and oils to deliver fast-drying sunscreens. Antimicrobials such as benzoyl peroxide may also be added to the formulations and the formulations may be useful as an acne medication. The systems of this invention may also be formulated with barrier compounds to form barrier creams and lotions. Materials which may be added to provide barrier protection for use as skin barriers to protect against diaper rash include but are not limited to 0.1 to 60% aldioxa, allantoin, aluminum acetate, aluminum hydroxide, bismuth subnitrate, boric acid, calamine, cellulose (microporous), cholecalciferol, cocoa butter, cod liver oil (in combination), colloidal oatmeal, cysteine hydrochloride, dexpanthenol, dimethicone, glycerin kaolin, lanolin (in combination), live yeast cell derivative, mineral oil, peruvian balsam, peruvian balsam oil, petrolatum, protein hydrolysate (1-leucine, 1-isoleucine, 1-methionine, 1-phenylalanine, and 1-tyrosine), racemethionine, shark liver oil, sodium bicarbonate, sulfur, talc, tannic acid, topical starch, vitamin A, white petrolatum, zinc acetate, zinc carbonate and zinc oxide. Formulations are also contemplated containing antifungal agents for treating fungal infections of the skin such as athlete's foot and the like.

Since many of the compositions of the present invention contain pharmaceutical agents and/or antimicrobials it is important that they be dispensed in an efficacious and precise amount. The compositions of the present invention can be dispensed in a discreet, substantially uniform amount using the dispensers disclosed in Applicants' Assignee's copending U.S. patent application Ser. Nos. 08/668,198, filed Jun. 21, 1996, entitled "Dispenser for Antimicrobial Liquids" and 08/668,270, filed Jun. 21, 1996 entitled "Drip Resistant Nozzle for a Dispenser".

Methods of Preparation

The compositions of the present invention may be prepared by a variety of techniques. For example, the process can often be as simple as adding the thickener system to the hydroalcoholic solvent at a temperature above the melting point of the surfactant(s), mixing briefly and cooling, although the heating step may not be required. It is often beneficial to hold the mixture at an elevated temperature to ensure complete reaction and association. To ensure a composition of maximum stability the components are preferably subjected to high shear (e.g., homogenized) for a limited time period while above the melting point of the thickener system followed by low shear mixing while cooling. The system should be mixed under high shear long enough to ensure complete mixing and association, however, excessive high shear mixing may result in decreased viscosity and stability.

The cooling rate may be important depending on the particular thickener system. Certain thickener systems can be homogenized and then allowed to cool slowly, however, rapid cooling appears to work well for most systems.

The order of adding the components may also affect the stability and viscosity of the system. In general it works well to melt the surfactant(s) of the thickener system with aqueous-insoluble emollients together in one vessel. The hydroalcoholic solvent, ionizable polymer, and any aqueous miscible emollients are mixed in a second vessel. Both components are heated above the melting temperature of the thickener system. The hot liquid components are mixed together rapidly followed by approximately 1 to 5 minutes of homogenization for typical batches under 500 grams. While still low in viscosity the system is stirred using moderate agitation and cooled. It is also possible to add the molten thickener system along with any solvent insoluble emollients to hot water (i.e., water at a temperature above the melting temperature) followed by high shear mixing and subsequent dilution with alcohol. The processing variables including amount and intensity of high shear mixing, rate of cooling, and order of addition are easily determined by one skilled in the art.

For associative systems based on acid-base reactions to form the polymer/surfactant complex, it is useful to monitor pH change to follow the reaction and insure complete reaction. In this way, one of skill in the art can determine if an ionically associated complex is formed.

TEST METHODS

Viscosity

In the following Examples (except where indicated) viscosity was measured at 23° C. at ambient pressure using a Brookfield LVDV-I$^+$ viscometer equipped with a model D Brookfield heliopath and T spindles B-F. The spindle and speed was chosen for each particular sample such that the viscometer was operating in the middle of its range. All samples were allowed to equilibrate at 23° C. for 24 hours prior to measurement. Preferably the viscosity is taken at the lowest speed possible while staying within 20–80% of the viscometer range and more preferably between 30–70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles. The following table outlines preferred spindles for various sample viscosities.

| Sample Viscosity | T Spindle to Use |
|---|---|
| 1,000–100,000 | B |
| 10,000–200,000 | C |
| 50,000–500,000 | D |
| 100,000–1,250,000 | E |
| 500,000–3,000,000 | F |

The viscosity of each sample was taken as the highest relatively stable reading achieved on the first path the spindle traversed using the heliopath adapter.

Stability

The stability of samples was measured 24 hours after conditioning at ambient conditions by placing 12 ml of a formulation that formed a lotion/cream in a 15 ml graduated centrifuge tube. The tube was then centrifuged in a Labofuge B (Heraeus Sepatech GmbH, Model 2650, rotor 2150 and buckets #2101) at 2000 rpm (1545×g when measured at the longitudinal midpoint of the sample tube) for 30 minutes at 23° C. Stability is recorded as a volume percent separation in the Examples below.

Melt Temperature ($T_m$)

The melt temperature was measured by placing approximately 15 grams sample in a 25 cc sealed glass vial and placing the vial in a water bath. The temperature of the bath was increased periodically in discrete increments and the contents checked after approximately 1 hour at a given temperature. The melt temperature was taken as the temperature at which the mixture became very low in viscosity.

Cosmetic Properties/Tactile Testing

For use in presurgical disinfection the compositions of this invention are preferably formulated with emollients to achieve a moisturized but relatively dry feel. Lotions with excessive emollients tend to be perceived as greasy and can result in excessive clumping of the powder under surgical gloves. The preferred formulations of this invention do not provide a tacky or sticky feel even in high humidity environments throughout the application process. The invention formulations preferably yield a smooth, soft, non-tacky, and moisturized feeling.

EXAMPLES

The following Examples are provided to illustrate the invention and are not intended to limit the scope of the invention.

Example 1

Polyhydrogenphosphate Polymer with Tertiary Amine Surfactant

A dimethicone copolyol hydrogen phosphate polymer available as "PECOSIL PS-100" (was approximately 98% active) from Phoenix Chemical Inc. of Sommerville, N.J., was combined in various ratios with behenamidopropyldimethylamine (available as "INCROMINE BB" from Croda Inc. of Parsippany, N.J.). The polymer was dissolved in the hydroalcoholic solvent (ethanol/water of the ratios indicated in the table below) and heated to 70° C. The "INCROMINE BB" was heated in a separate vessel to 70° C. The hot polymer solution was added to the surfactant while subjecting the contents to high shear on a Silverson L4R homogenizer available from Silverson Machines, Waterside England. Once the addition was complete the contents were homogenized on the highest setting for 30 seconds, sealed, and heated in an oven at 60° C. for one hour. The contents were sheared on high for an additional 30 seconds before allowing the composition to cool to ambient temperature. All compositions produced appeared as an opaque white lotion/cream. After sitting for at least 24 hours, the viscosity and stability were determined as described herein. The following results were obtained.

| Polymer wt. (g) | Surfactant wt. (g) | Solvent wt. (g) | Ethanol/water wt. ratio | Viscosity (cps) | Stability (%) | $T_m$ (° C.) |
|---|---|---|---|---|---|---|
| 6 | 2 | 92 | 20:80 | 100,000 | — | — |
| 6 | 2 | 92 | 40:60 | 75,000 | — | — |
| 6 | 3 | 91 | 40:60 | 106,000 | — | — |
| 12 | 6 | 82 | 40:60 | 197,000 | — | — |
| 8 | 4 | 88 | 40:60 | 62,000/ 2.1 | 38–43 | |
| 10 | 6 | 84 | 40:60 | 25,000 | 4.2 | 28–43 |
| 12 | 6 | 82 | 40:60 | 100,000 | 33.3 | 38–43 |
| 8 | 2.6 | 89.4 | 40:60 | unstable, precipitates | | |
| 8 | 1.1 | 91.9 | 40:60 | unstable, precipitates | | |
| 8 | 1.6 | 91.4 | 40:60 | unstable, precipitates | | |

Example 2
Polysulfonic Acid Polymer with Tertiary Amine Surfactant

A sulfonic acid polymer available from Henkel as HSP-1180 (2-methyl-2-((oxo-2-propenyl)amino)-1-propane sulfonic acid, which was supplied as a solution in water, the polymer concentration was approximately 14% by weight) was combined in various ratios with a behenamidopropyldimethylamine (available as "INCROMINE BB" from Croda Inc., Parsippany N.J.). The procedure of Example 1 was used with the following results. All compositions produced appeared as an opaque white lotion/cream.

| Polymer wt. (g) | Emulsifier wt. (g) | Solvent wt. (g) | Ethanol/water wt. ratio | Viscosity (cps) | Stability (%) | $T_m$ (° C.) |
|---|---|---|---|---|---|---|
| 3 | 6 | 91 | 40:60 | 39,000 | 4.2 | — |
| 3 | 6 | 91 | 50:50 | 9,000 | 8.3 | 42 |
| 3 | 7 | 90 | 40:60 | 25,000 | 8.3 | — |
| 6 | 6 | 88 | 40:60 | unstable, precipitates | | |
| 8 | 2.7 | 89.3 | 40:60 | unstable, precipitates | | |
| 8 | 1.9 | 90.1 | 40:60 | unstable, precipitates | | |
| 8 | 0.8 | 91.2 | 40:60 | unstable, precipitates | | |

Example 3
Tertiary Amine Polymer with Carboxylic Acid Emulsfier

A terpolymer of methylmethacrylate, dimethylaminoethylmethacrylate, and a polystyrene macromer was prepared according to the following procedure. To a one liter glass bottle were added 225.0 grams of ethyl acetate, 137.5 grams of methyl methacrylate, 115.5 grams of dimethylaminoethyl methacrylate, 0.825 gram of azobisisobutyronitrile (AIBN), which is available as "VAZO 64" from E.I. duPont deNemors of Wilmington, Del., 22.0 grams of polystyrylethyl methacrylate having a molecular weight of about 10,000, which is available from Sartomer of Exton, Pa., or Polymer Chemistry Innovations of Tucson, Ariz. The mixture was deoxygenated by purging with one liter per minute nitrogen for two minutes. The bottle was sealed and placed in a rotating water bath at 55° C. for 24 hours. Ethyl acetate (220.0 grams) was added to dilute the polymer to 36.65% solids and 52,500 cps. The inherent viscosity was measured as 0.685 dl/g in ethyl acetate at a concentration of 0.2 g/dl. The test procedure and apparatus used are described in "Textbook of Polymer Science"; F. W. Billmeyer, Ed.; Wiley-Interscience, NY; 2nd Edition; 84–85 (1971).

This terpolymer was combined in various ratios with stearoyl sarcoine surfactant (available as "HAMPOSYL S" from Hampshire Chemical Corp., Lexington, Mass.). A 2.8% by weight polymer solution in ethanol was prepared by heating at 70° C. for several hours. A 10% by weight solution of surfactant was prepared by mixing 13 grams of "HAMPOSYL S" in 117 grams of ethanol/water in the weight ratios shown in the following table. The following results were observed:

| Polymer soln (g) | Surfactant soln (g) | Surfactant Polymer wt. ratio | Ethanol/water wt. ratio | Wt. % Polymer | Composition Appearance |
|---|---|---|---|---|---|
| 10.71 | 0 | 0 | 100/0 | 2.8 | cloudy |
| 10.71 | 0.3 | 0.10 | 97.5/2.5 | 2.72 | clear, no thickening |
| 10.71 | 2.5 | 0.83 | 82.2/17.8 | 2.27 | some thickening observed immediately, standing gels |
| 10.71 | 1.5 | 0.5 | 88.5/11.5 | 2.46 | thickens to a gel like consistency |
| 10.71 | 2.25 | 0.75 | 83.7/16.3 | 2.31 | thickens to a gel like consistency |
| 10.71 | 3.0 | 1.0 | 79.4/20.6 | 2.18 | thickens to a gel like consistency |
| 10.71 | 9.0 | 3.0 | 56.2/43.8 | 1.52 | thickens to a gel like consistency |

While in accordance with the patent statutes, description of the preferred weight fractions, processing conditions, and product usages have been provided, the scope of the invention is not intended to be limited thereto or thereby. Various modifications and alterations of the present invention will be apparent to those skilled in the art without departing from the scope and spirit of the present invention. The Examples described in this application are illustrative of the possibilities of varying the type, quantity and ratio of components as well as the methods for making compositions of the present invention. All patents, patent applications, and publications cited herein are incorporated by reference in their entirety, as if individually incorporated.

What is claimed is:

1. A hydroalcoholic composition comprising:
   (a) a lower alcohol and water in a weight ratio of at least about 20:80;
   (b) a thickener system comprising a complex of at least one charged polymer selected from the group of a polyhydrogen phosphate, a polysulfonic acid, a polycarboxylic acid, a polyamine, and mixtures thereof, and at least one oppositely charged surfactant of the formula $(R)_a(L)_b$ wherein "R" represents a hydrophobic group, "L" represents a hydrophilic group having at least one ionic group, and "a" and "b" are independently 1–4;

wherein:
   (A) the hydrophobic group of the charged surfactant comprises an alkyl group of at least 16 carbon atoms, an alkenyl group of at least 16 carbon atoms, or an aralkyl or an aralkenyl group of at least 20 carbon atoms;
   (B) the hydrophilic group of at least one surfactant comprises at least one primary, secondary, or tertiary amine, a guatemary amine, an acidic group, or an anionic group derived from an acidic group or salt of an acidic group on the surfactant, wherein the acidic group is selected from the group of —$OSO_2OH$, —$SO_2OH$, (—O)$_2$P(O)OH, —OP(O)(OH)$_2$, —OP(O)(OH)(O$^-$M$^+$), —PO(OH)$_2$, —PO(OH)(O$^-$M$^+$), –$CO_2H$, and mixtures thereof; wherein M$^+$ is a positively charged counterion and is selected from the group consisting of hydrogen, sodium, potassium, lithium, ammonium, calcium, magnesium or N$^+$R'$_4$ where each R' is independently an alkyl group of 1 to 4 carbon atoms, optionally substituted with N, O, or S atoms; and (C) the polymer and surfactant are selected in amounts such that:
  (i) the composition does not separate more than about 10% by volume after centrifugation at 1545×g for 30 minutes and has a viscosity greater than that of the same composition with either the polymer or the surfactant absent; and
  (ii) the composition has a viscosity of at least about 4,000 centipoise at 23° C., when free of auxiliary thickeners.

2. The composition of claim 1 wherein the polymer and emulsifier are selected such that the composition, when free of auxiliary thickeners, has a viscosity of at least about 20,000 centipoise at 23° C.

3. The composition of claim 1 wherein the thickener system is present in an amount of less than about 12% by weight, based on the total weight of the composition.

4. The composition of claim 3 wherein the thickener system is present in an amount of less than or equal to about 6% by weight, based on the total weight of the composition.

5. The composition of claim 1 wherein the thickener system comprises at least one surfactant that is solid at ambient temperature.

6. The composition of claim 5 wherein the thickener system comprises at least two surfactants, each surfactant being present in an amount of at least about 0.05% by weight, based on the total weight of the composition.

7. The composition of claim 1 wherein the surfactant is present in an amount sufficient to ionically associate with at least about 3 mole-% of the ionic groups of the polymer molecules.

8. The composition of claim 7 wherein the surfactant is present in an amount sufficient to ionically associate with at least about 10 mole-% of the ionic groups of the polymer molecules.

9. The composition of claim 1 wherein the hydrophobic group of at least one surfactant includes a saturated straight chain hydrocarbon group of at least 16 carbon atoms.

10. The composition of claim 1 wherein the alcohol to water ratio is at least about 35:65.

11. The composition of claim 10 wherein the alcohol to water ratio is within a range of about 40:60 to about 95:5.

12. The composition of claim 1 wherein the charged polymer of the thickener system comprises hydrophobic side chains.

13. The composition of claim 12 wherein the hydrophobic side chains are selected from the group of alkyl side chains having at least 16 carbon atoms, polystyrene side chains, and mixtures thereof.

14. The composition of claim 1 further including a secondary antimicrobial agent.

15. The composition of claim 14 wherein said antimicrobial agent is selected from the group of CHG, iodine, triclosan, PCMX, and mixtures thereof.

16. The composition of claim 1 further comprising at least one emollient.

17. The composition of claim 16 wherein said emollient is selected from the group of a wax, an oil, a humectant, and mixtures thereof.

18. The composition of claim 1 wherein the lower alcohol is selected from the group of ethanol, 2-propanol, n-propanol, and mixtures thereof.

19. The composition of claim 1 further comprising an additive selected from the group of a stabilizer, a salt, a propellant, and mixtures thereof.

20. The composition of claim 1 further comprising a pharmaceutical agent.

21. The composition of claim 20 which is suitable for the enhancement of the transdermal delivery of the pharmaceutical agent.

22. The composition of claim 1 which is in the form of a lotion.

23. A hydroalcoholic composition preparable by combining components comprising:
  (a) a lower alcohol and water in a weight ratio of at least about 20:80;
  (b) at least one ionizable polymer selected from the group of a polyhydrogen phosphate, a polysulfonic acid, a polycarboxylic acid, a polyamine, and mixtures thereof; and
  (c) at least one ionizable surfactant of the formula $(R)_a(L)_b$ wherein "R" represents a hydrophobic group, "L" represents a hydrophilic group having at least one ionic group, and "a" and "b" are independently 1–4,
  wherein:
    (A) the hydrophobic group of the charged surfactant comprises an alkyl group of at least 16 carbon atoms, an alkenyl group of at least 16 carbon atoms, or an aralkyl or an aralkenyl group of at least 20 carbon atoms;
    (B) the hydrophilic group of at least one surfactant comprises at least one primary, secondary, or tertiary amine, a quaternary amine, an acidic group, or an anionic group derived from an acidic group or salt of an acidic group on the surfactant, wherein the acidic group is selected from the group of $—OSO_2OH$, $—SO_2OH$, $(—O)_2P(O)OH$, $—OP(O)(OH)_2$, $—OP(O)(OH)(O^-M^+)$, $—PO(OH)_2$, $—PO(OH)(O^-M^+)$, $—CO_2H$, and mixtures thereof; wherein $M^+$ is a positively charged counterion and is selected from the group consisting of hydrogen, sodium, potassium, lithium, ammonium, calcium, magnesium or $N^+R'_4$ where each R' is independently an alkyl group of 1 to 4 carbon atoms, optionally substituted with N, O, or S atoms; and
    (C) the polymer and surfactant are selected in amounts such that:
      (i) the hydroalcoholic composition does not separate more than about 10% by volume after centrifugation at 1545×g for 30 minutes and has a viscosity greater than that of the same composition with either the polymer or the surfactant absent; and
      (ii) the hydroalcoholic composition has a viscosity of at least about 4,000 centipoise at 23° C., when free of auxiliary thickeners.

24. The composition of claim 22 wherein the ionizable polymer comprises at least three basic groups per molecule.

25. The composition of claim 24 wherein the basic groups comprise primary, secondary, or tertiary amines.

26. The composition of claim 22 wherein the ionizable polymer comprises at least three acidic groups per molecule.

27. The composition of claim 22 further comprising a pharmaceutical agent.

28. The composition of claim 27 which is suitable for the enhancement of the transdermal delivery of the pharmaceutical agent.

29. The composition of claim 22 which is in the form of a lotion.

30. The composition of claim 22 wherein the alcohol to water ratio is at least about 35:65.

31. A method of preparing a hydroalcoholic composition, the method comprising:
  heating an ionizable surfactant at a sufficient temperature to melt the surfactant; wherein the ionizable surfactant is of the formula $(R)_a(L)_b$ wherein "R" represents a hydrophobic group, "L" represents a hydrophilic group having at least one ionic group, and "a" and "b" are independently 1–4; wherein the hydrophobic group of the charged surfactant comprises an alkyl group of at least 16 carbon atoms, an alkenyl group of at least 16 carbon atoms, or an aralkyl or an aralkenyl group of at least 20 carbon atoms, and the hydrophilic group of at least one surfactant comprises at least one primary, secondary, or tertiary amine, a quaternary amine, an acidic group, or an anionic group derived from an acidic group or salt of an acidic group on the surfactant, wherein the acidic group is selected from the group of —OSO$_2$OH, —SO$_2$OH, (—O)$_2$P(O)OH, —OP(O)(OH)$_2$, —OP(O)(OH)(O$^-$M$^+$), —PO(OH)$_2$, —PO(OH)(O$^-$M$^+$), —CO$_2$H, and mixtures thereof; wherein M$^+$ is a positively charged counterion and is selected from the group consisting of hydrogen, sodium, potassium, lithium, ammonium, calcium, magnesium or N$^+$R'$_4$ where each R' is independently an alkyl group of 1 to 4 carbon atoms, optionally substituted with N, O, or S atoms;

combining an ionizable polymer selected from the group of a polyhydrogen phosphate, a polysulfonic acid, a polycarboxylic acid, a polyamine, and mixtures thereof with a solvent system comprising water and a lower alcohol;

combining the melted surfactant with the polymer/solvent system mixture to form a hydroalcoholic composition comprising a lower alcohol and water in a weight ratio of at least about 20:80; a thickener system comprising a complex of at least one charged polymer and at least one oppositely charged surfactant, wherein the polymer and surfactant are selected in amounts such that the composition does not separate more than about 10% by volume after centrifugation at 1545×g for 30 minutes and has a viscosity greater than that of the same composition with either the polymer or the surfactant absent, and has a viscosity of at least about 4,000 centipoise at 23° C., when free of auxiliary thickeners.

32. A hydroalcoholic composition prepared from the method of claim 23.

33. The hydroalcoholic composition of claim 1 wherein;
(a) the surfactant is selected from the group of an amine, a hydrogen phosphate, a hydrogen sulfate, a carboxylic acid, and mixtures thereof, and
(b) the polymer is selected from the group of a polyhydrogen phosphate, a polysulfonic acid, a polycarboxylic acid, a polyamine, and mixtures thereof.

34. The hydroalcoholic composition of claim 23 wherein;
(a) the surfactant is selected from the group of an amine, a hydrogen phosphate, a hydrogen sulfate, a carboxylic acid, and mixtures thereof; and
(b) the polymer is selected from the group of a polyhydrogen phosphate, a polysulfonic acid, a polycarboxylic acid, a polyamine, and mixtures thereof.

35. A hydroalcoholic composition comprising:
(a) a lower alcohol and water in a weight ratio of at least about 20:80;
(b) a thickener system comprising a complex of at least one charged polymer selected from the group of a polyhydrogen phosphate, a polysulfonic acid, a polycarboxylic acid, a polyamine, and mixtures thereof, and at least one oppositely charged surfactant of the formula $(R)_a(L)_b$ wherein "R" represents a hydrophobic group, "L" represents a hydrophilic group having at least one ionic group, and "a" and "b" are independently 1–4;

wherein:
(A) the hydrophobic group of the charged surfactant comprises an alkyl group of at least 16 carbon atoms, an alkenyl group of at least 16 carbon atoms, or an aralkyl or an aralkenyl group of at least 20 carbon atoms;
(B) the hydrophilic group of at least one surfactant comprises at least one ionic hydrophilic group and at least one nonionic hydrophilic group selected from the group of an amide group, an ester group, an alcohol group, a sorbitan group, a polyglyceryl group, a polyglucoside group, a polyethylene glycol group, and mixtures thereof; and
(C) the polymer and surfactant are selected in amounts such that:
(i) the composition does not separate more than about 10% by volume after centrifugation at 1545×g for 30 minutes and has a viscosity greater than that of the same composition with either the polymer or the surfactant absent; and
(ii) the composition has a viscosity of at least about 4,000 centipoise at 23° C., when free of auxiliary thickeners.

36. The composition of claim 35 wherein the polymer and emulsifier are selected such that the composition, free of auxiliary thickeners, has a viscosity of at least about 20,000 centipoise at 23° C.

37. The composition of claim 35 wherein the thickener system is present in an amount of less than about 12% by weight, based on the total weight of the composition.

38. The composition of claim 35 wherein the alcohol to water ratio is within a range of about 40:60 to about 95:5.

39. The composition of claim 35 further including a secondary antimicrobial agent.

40. The composition of claim 35 further comprising a pharmaceutical agent.

41. A hydroalcoholic composition preparable by combining components comprising:
(a) a lower alcohol and water in a weight ratio of at least about 20:80;
(b) at least one ionizable polymer selected from the group of a polyhydrogen phosphate, a polysulfonic acid, a polycarboxylic acid, a polyamine, and mixtures thereof; and
(c) at least one ionizable surfactant of the formula $(R)_a(L)_b$ wherein "R" represents a hydrophobic group, "L" represents a hydrophilic group having at least one ionic group, and "a" and "b" are independently 1–4;

wherein:
(A) the hydrophobic group of the charged surfactant comprises an alkyl group of at least 16 carbon atoms, an alkenyl group of at least 16 carbon atoms, or an aralkyl or an aralkenyl group of at least 20 carbon atoms;
(B) the hydrophilic group of at least one surfactant comprises at least one ionic hydrophilic group and at least one nonionic hydrophilic group selected from the group of an amide group, an ester group, an alcohol group, a sorbitan group, a polyglyceryl group, a polyglucoside group, a polyethylene glycol group, and mixtures thereof; and
(C) the polymer and surfactant are selected in amounts such that:
(i) the hydroalcoholic composition does not separate more than 10% by volume after centrifugation at 1545×g for 30 minutes and has a viscosity greater than that of the same composition with either the polymer or the surfactant absent; and (ii) the hydroalcoholic composition has a viscosity of at least about 4,000 centipoise at 23° C., when free of auxiliary thickeners.

42. The composition of claim 41, further comprising a pharmaceutical agent.

43. The composition of claim 41, wherein the alcohol to water ratio is within a range of about 40:60 to about 95:5.

44. A method of preparing a hydroalcoholic composition, the method comprising: heating an ionizable surfactant at a sufficient temperature to melt the surfactant; wherein the ionizable surfactant is of the formula $(R)_a(L)_b$ wherein "R" represents a hydrophobic group, "L" represents a hydrophilic group having at least one ionic group, and "a" and "b" are independently 1–4; wherein the hydrophobic group of the charged surfactant comprises an alkyl group of at least 16 carbon atoms, an alkenyl group of at least 16 carbon atoms, or an aralkyl or an aralkenyl group of at least 20 carbon atoms, and the hydrophilic group of at least one surfactant comprises at least one ionic hydrophilic group and at least one nonionic hydrophilic group selected from the group of an amide group, an ester group, an alcohol group, a sorbitan group, a polyglyceryl group, a polyglucoside group, a polyethylene glycol group, and mixtures thereof;

combining an ionizable polymer selected from the group of a polyhydrogen phosphate, a polysulfonic acid, a polycarboxylic acid, a polyamine, and mixtures thereof with a solvent system comprising water;

combining the melted surfactant with the polymer/solvent system mixture to form a hydroalcoholic composition comprising a lower alcohol and water in a weight ratio of at least about 20:80; a thickener system comprising a complex of at least one charged polymer and at least one oppositely charged surfactant, wherein the polymer and surfactant are selected in amounts such that the composition does not separate more than about 10% by volume after centrifugation at 1545×g for 30 minutes and has a viscosity greater than that of the same composition with either the polymer or the surfactant absent, and has a viscosity of at least about 4,000 centipoise at 23° C., when free of auxiliary thickeners.

45. The method of claim 44 wherein the solvent system further includes a lower alcohol.

46. A hydroalcoholic composition prepared from the method of claim 44.

* * * * *

UNITED STATES PATENT AND TRADEMARK OFFICE
CERTIFICATE OF CORRECTION

PATENT NO.: 5,908,619
DATED: 1 June 1999
INVENTOR(S): Matthew T. Scholz

It is certified that error appears in the above-identified patent and that said Letters Patent is hereby corrected as shown below:

At column 14, line 61, please delete "comeum" and insert therefor -- corneum --.

At column 14, line 64, please delete "comeum" and insert therefor -- corneum --.

At column 14, line 64, please delete "comeum" and insert therefor -- corneum --.

At column 18, line 7, please delete "chiorofluorocarbons" and insert therefor -- chlorofluorocarbons --.

At column 19, line 38, please delete "tetrahydroftifryl" and insert therefor -- tetrahydrofurfuryl --.

At column 22, line 58, under the heading Viscosity (cps), please delete "62,000/2.1" and insert therefor -- 62,000 --.

At column 22, line 58, under the heading Stability (%), please delete "38-43" and insert therefor -- 2.1 --.

At column 22, line 58, under the heading Tm (°C.), please delete " " and insert therefor -- 38-43 --.

At column 24, line 14, under the heading Composition Appearance, please delete " standing gels" and insert therefor -- on standing gels --.

At column 24, line 55, please delete "guatemary" and insert therefor -- quaternary --.

Signed and Sealed this

First Day of May, 2001

*Attest:*

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 5,908,619
DATED : June 1, 1999
INVENTOR(S) : Matthew T. Scholz

It is certified that error appears in the above-identified patent and that said Letters Patent is hereby corrected as shown below:

Column 14,
Lines 61, 64 and 66, please delete "comeum" and insert therefor -- corneum --.

Column 18,
Line 7, please delete "chiorofluorocarbons" and insert therefor -- chlorofluorocarbons --.

Column 19,
Line 38, please delete "tetrahydroftifryl" and insert therefor -- tetrahydrofurfuryl --.

Column 22,
Line 58, under the heading Viscosity (cps), please delete "62,000/2.1" and insert therefor -- 62,000 --.
Line 58, under the heading Stability (%), please delete "38-43" and insert therefore -- 2.1 --.
Line 58, under the heading Tm (°C), please delete " " and insert therefor -- 38-43 --.

Column 24,
Line 14, under the heading Composition Apperance, please delete "standing gels" and insert therefor -- on standing gels --.
Line 55, please delete "guatermary" and insert therefor -- quaternary --.

Signed and Sealed this

Eleventh Day of December, 2001

*Attest:*

NICHOLAS P. GODICI
*Attesting Officer*   Acting Director of the United States Patent and Trademark Office